United States Patent [19]

Epstein et al.

[11] 4,263,305
[45] Apr. 21, 1981

[54] NOVEL PYRIDINIUMALDOXIMES HAVING MICELLAR CHARACTERISTICS

[75] Inventors: Joseph Epstein, Baltimore, Md.; Nicholas S. Bodor, Lawrence, Kans.

[73] Assignee: Interx Research Corporation, Lawrence, Kans.

[21] Appl. No.: 19,660

[22] Filed: Mar. 12, 1979

[51] Int. Cl.$^3$ .................. A61K 31/15; A61K 31/435; C07D 213/76
[52] U.S. Cl. ..................................... 424/263; 546/338
[58] Field of Search ......................... 546/338; 424/263

[56] References Cited

U.S. PATENT DOCUMENTS

| 2,816,113 | 12/1957 | Wilson et al. | 546/338 |
|---|---|---|---|
| 3,140,289 | 7/1964 | Ellin et al. | 546/338 |

FOREIGN PATENT DOCUMENTS 936062  9/1963  United Kingdom ..................... 546/338

OTHER PUBLICATIONS de Jong et al., Croatica Chemica/Acta, vol. 47, pp. 383 to 391, (1975).
Ellin et al., J. Pharm. Sci., vol. 53, No. 9, pp. 995–1007, (1964).
Wilson et al., Arch. Biochem. Biophys. vol. 77, pp. 286–296, (1958).
Wilson, Biochimica et Biophysica Acta, vol. 27, pp. 196–199, (1958).

Primary Examiner—John D. Randolph
Attorney, Agent, or Firm—Burns, Doane, Swecker & Mathis

[57] ABSTRACT

Novel pyridiniumaldoximes having micellar characteristics are useful in the deactivation of organophosphates. Fast and effective detoxification of areas and equipment contaminated with organophosphate pesticides and insecticides results from use of the reagents.

20 Claims, No Drawings

NOVEL PYRIDINIUMALDOXIMES HAVING MICELLAR CHARACTERISTICS

BACKGROUND OF THE INVENTION

1. Field of the Invention

The invention provides novel pyridiniumaldoximes having micellar characteristics which are useful in the deactivation of known organophosphate pesticides and insecticides.

2. Description of the Prior Art

Compounds of the formula

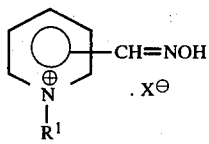

wherein $R^1$ is a $C_1-C_4$ alkyl group and $X^\ominus$ represents an anion derived from a pharmaceutically acceptable acid addition salt have been previously described. Of these, the best known are 1-methyl pyridinium-2-aldoxime iodide ("2-PAM") and 1-methyl pyridinium-3-aldoxime iodide ("3-PAM"). 2-PAM has been used therapeutically as a cholinesterase reactivator in attempts to overcome some of the effects of poisoning with anticholinesterases such as organophosphorus insecticides.

SUMMARY OF THE INVENTION

It has now been found that compounds structurally related to those discussed above exhibit micellar characteristics which make them surprisingly useful in the deactivation of organophosphates. More particularly, it has been found that the use of reagents of the formula

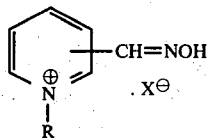

wherein R is an organic residue capable of providing micellar characteristics to the molecule and $X^\ominus$ is an anion derived from a non-toxic inorganic or organic acid, results in the fast and effective detoxification of areas and equipment contaminated with organophosphate pesticides and insecticides. Rapid detoxification of contaminated portions of the environment (e.g. areas, cans and equipment) helps avoid toxic exposure of humans and animals to the organophosphates and also makes possible the safe recycling of containers and other utensils and equipment.

DETAILED DESCRIPTION OF THE INVENTION

In order to provide the necessary micellar characteristics, the organic residue represented by R in formula (I) should comprise a chain at least 7 atoms in length. The chain will ordinarily be an acyclic hydrocarbon, which may be saturated or unsaturated. Optionally, one or more hetero atoms (e.g. S, N or O) may be present as one or more of the requisite 7 atoms in the chain. In addition, the chain may bear one or more substituents, which can be aliphatic, cycloaliphatic or aromatic groups, any of which may optionally contain one or more hetero atoms.

In a preferred embodiment, the present invention provides a novel group of compounds of formula (I) wherein R is a radical of the type -(alkylene-O)$_n$-alkyl wherein n is a number from 0 to 4 inclusive and the alkylene and alkyl portions together contain from 6 to 25 carbon atoms, with the proviso that R has a total of at least 7 atoms in its longest chain. Preferably, when n is a number greater than zero, the oxygen atom will be separated from the pyridine ring system by an alkylene bridge of at least 2 carbon atoms.

Representative of the alkyl radicals which are encompassed by R (i.e. the compounds wherein n is zero] are n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-heneicosyl, n-docosyl, n-tricosyl, n-tetracosyl, and n-pentacosyl, as well as the corresponding branched-chain groups containing 8 to 25 carbon atoms and having at least 7 carbon atoms in their longest chain.

Representative of the alkoxyalkyl radicals encompassed by R [i.e. the compounds wherein n is 1] are methoxypentyl, methoxyhexyl, methoxyheptyl, methoxyoctyl, methoxynonyl, methoxydecyl, ethoxybutyl, ethoxypentyl, ethoxyhexyl, ethoxyheptyl, ethoxyoctyl, ethoxynonyl, propoxypropyl, propoxybutyl, propoxypentyl, propoxyhexyl, propoxyheptyl, propoxyoctyl, butoxyethyl, butoxypropyl, butoxybutyl, butoxypentyl, butoxyhexyl, butoxyheptyl, pentoxyethyl, pentoxypropyl, pentoxybutyl, pentoxypentyl, pentoxyhexyl and like straight-chain alkoxyalkyl groups containing 6 to 25 carbon atoms, as well as the corresponding branched-chain groups containing 7 to 25 carbon atoms and having at least 7 atoms (i.e., the oxygen atom and a total of at least 6 carbon atoms) in their longest chain.

Exemplary of radicals wherein n is greater than one is the —(CH$_2$CH$_2$O)$_4$CH$_2$CH$_3$ radical.

In another preferred embodiment of the invention, the oxime group (—CH=NOH) in formula (I) is attached at the 3-position of the pyridine ring.

An especially preferred group of compounds provided by the present invention consists of those novel pyridiniumaldoximes which can be represented by the formula

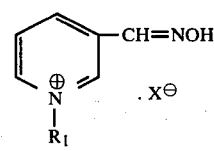

wherein $R_1$ is a radical of the type —(alkylene-O)$_n$-alkyl wherein n is a number from 0 to 4 inclusive and the alkylene and alkyl portions together contain from 6 to 25 carbon atoms, with the proviso that R has a total of at least 7 atoms in its longest chain, and $X^\ominus$ is as hereinabove defined.

In formulas (I) and (II) above, the non-toxic anions represented by $X^\ominus$ include, but are not limited to, those derived from inorganic acids such as hydriodic, hydrochloric, hydrobromic, sulfuric, sulfamic, phosphoric, and the like; and those derived from organic acids such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, toluenesulfonic, and related acids. Preferred salts are the halides (X being I, Cl or Br), the 5-sulfosalicylates, and the compounds wherein X is a radical of the formula —$R_2SO_3$ wherein $R_2$ is $C_1$–$C_{20}$ alkyl (e.g. methanesulfonates), phenyl, substituted phenyl, particularly alkyl-substituted phenyl (e.g. p-toluenesulfonates), or naphthyl.

The compounds of the present invention can be prepared in the manner discussed hereinbelow. Although this discussion will be limited to the preparation of the preferred compounds of the invention wherein R is an alkyl radical containing 7 to 25 carbon atoms and having at least 7 carbon atoms in its longest chain, it will be understood that the remaining compounds of formulas (I) and (II) can be prepared in an analogous manner to that set forth below or by other methods known in the art.

Preparation of the instant compounds proceeds by reacting a tertiary amine of the formula

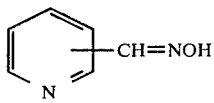

with an appropriate alkylating agent, followed by, when desired, an ion exchange procedure as described below.

The low reactivity of the tertiary amine to be quaternized generally requires the use of especially reactive alkylating agents such as the alkyl tosylates or alkyl halides (particularly the iodides). Under these circumstances, the alkylating agent used inherently determines the identity of the gegen ion in the quaternary salt. Thus, when the compounds of the invention wherein $X^\ominus$ is a less reactive species are desired, the alkylation step will be followed by an ion exchange procedure.

Exchange of the gegen ion in the quaternary salt can be accomplished using an anion exchange resin. This procedure involves conversion of the quaternary salt to its hydroxide form and subsequent neutralization using the conjugate acid of the desired base. However, it has been found that a different and generally more convenient procedure can be employed for the exchange of gegen ions in the quaternary salts. The general scheme of the exchange is depicted below:

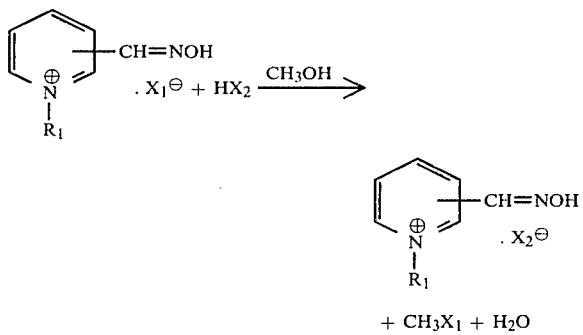

wherein $R_1$ is defined as before, $X_1$ is I, Br or Cl and $X_2$ is Br, Cl, —$CH_3SO_3$, —$C_6H_5SO_3$, —$CH_3C_6H_4SO_3$ or other suitable acid anion. Thus, a methanolic solution of an $HX_2$ acid will react with the quaternary ammonium halide to produce the methyl halide and the corresponding quaternary .$X_2$ salt. The methyl halide formed during the exchange is removed from the reaction mixture.

It is obvious that when quaternary iodides are the salts utilized in the anion exchange, the conjugate acids selected must not possess a sufficient oxidation potential to initiate the iodide⇌iodine oxidation. For example, treatment of quaternary iodides with methanolic solutions of sulfuric acid and nitric acid result in the formation of iodine. In addition, lack of anion exchange capability has been observed when organic acids of low p$K_a$ (e.g. acetic or lactic acid) are utilized. With these exceptions, the process has been found to be very effective and does not result in loss of alkyl group integrity in the quaternary salt.

In order to further illustrate the invention, the following specific examples are given, it being understood that same are intended only as illustrative and in nowise limitative.

EXAMPLE 1

Preparation of 1-n-Heptyl-3-Pyridiniumaldoxime Iodide 2.44 Grams of 3-pyridinealdoxime (0.02 mol) and 4.61 grams (0.02 mole) of n-heptyl iodide were combined and heated at 120°–130° C. for 45 minutes. The residue was cooled to room temperature and anhydrous ether was added. Trituration in anhydrous ether gave 4.5 grams (0.019 mol), 99% yield, of 1-n-heptyl-3-pyridiniumaldoxime iodide, m.p. 103°–105° C.; ir (KBr) 3220, 3020, 2920, 1640, 1500, 1410, 1280 and 970 cm$^{-1}$; pmr (d$^6$-DMSO) δ0.80 (t, 3H), 1.2 (bs, 8H), 1.9 (3H), 4.6 (t, 2H) and 7.8–9.15 (5H) ppm.

Anal. Calcd. for $C_{13}H_{21}IN_2O$: C, 44.84; H, 6.08; N, 8.05. Found: C, 44.76; H, 5.97; N, 7.94.

EXAMPLE 2

Preparation of 1-n-Dodecyl-3-Pyridiniumaldoxime Iodide

Repetition of the procedure described in Example 1 substituting an equivalent quantity of n-dodecyl iodide for the n-heptyl iodide there employed afforded 1-n-dodecyl-3-pyridiniumaldoxime iodide, m.p. 118°–120° C.; ir (KBr) 3180, 2920, 2840, 1500, 1470, 1290 and 1000 cm$^{-1}$; pmr (d$^6$-DMSO) δ0.8 (t, 3H), 1.2 (bs, 18H), 1.9 (2H), 4.7 (t, 2H) and 8.9–9.6 (5H) ppm.

Anal. Calcd. for $C_{18}H_{31}IN_2O$: C, 51.67; H, 7.47; N, 6.70. Found: C, 51.38; H, 7.41; N, 6.43.

EXAMPLE 3

Preparation of 1-n-Dodecyl-3-Pyridiniumaldoxime Chloride 4.18 Grams (0.01 mol) of 1n-dodecyl-3-pyridiniumaldoxime iodide were dissolved in 50 ml of methanol containing 8.6 grams (0.10 mol) of anhydrous hydrogen chloride. The solution was concentrated to 10 ml by distillation. The remaining solution was washed with ether to afford a crude product which was recrystallized from a mixture of acetone and petroleum ether to afford 1.98 grams (0.0061 mol), 61% yield, of 1-n-dodecyl-3-pyridiniumaldoxime chloride, m.p. 138°–140° C.; ir (KBr) 2900, 1620, 1500, 1300 and 1010 cm$^{-1}$; pmr (d$^6$-DMSO) δ12.4 (s, 1H), 9.5–8.0 (m, 5H), 4.7 (t, 2H) and 2.6–0.3 (m, 23H) ppm.

Anal. Calcd. for $C_{18}H_{31}ClN_2O$: C, 66.13; H, 9.56; N, 8.57; Cl, 10.85. Found: C, 66.17; H, 9.86; N, 8.26; Cl, 11.13.

EXAMPLE 4

Preparation of 1-n-Dodecyl-3-Pyridiniumaldoxime Bromide

The general procedure of Example 3 was repeated using hydrogen bromide in place of the hydrogen chloride. There were thus obtained 1.7 grams (0.0045 mol), 46% yield, of 1-n-dodecyl-3-pyridiniumaldoxime bromide, m.p. 141°–143° C.; ir (KBr) 3200, 2920, 1500, 1420, 1295 and 1000 cm$^{-1}$; pmr (d$^6$-DMSO) δ12.2 (s, 1H), 9.6–8.0 (m, 5H), 4.7 (t, 2H) and 2.7–0.7 (m, 23H) ppm.

Anal. Calcd. for $C_{18}H_{31}BrN_2O$: C, 58.21; H, 8.41; N, 7.55; Br, 21.52. Found: C, 58.28; H, 8.47; N, 7.47; Br, 21.66.

EXAMPLE 5

Preparation of 1-n-Dodecyl-3-Pyridiniumaldoxime Methanesulfonate

The procedure described in Example 3 was substantially repeated, except that methanesulfonic acid was employed in place of the hydrogen chloride. There were thus obtained 1.7 grams (0.0045 mol), 45% yield, of the desired 1-n-dodecyl-3-pyridiniumaldoxime methanesulfonate, m.p. 118°–120° C.; ir (KBr) 3250, 2900, 2800, 1500, 1290, 1185, 1060, 1000, 785 and 680 cm$^{-1}$; pmr (CDCl) δ9.4–8.0 (m, 5H), 4.8 (t, 2H), 2.8 (s, 3H) and 2.3–0.7 (m, 23H) ppm.

Anal. Calcd. for $C_{19}H_{34}N_2O_9S$: C, 59.02; H, 8.88; N, 7.25. Found: C, 58.98; H, 8.80; N, 7.25.

EXAMPLE 6

Preparation of 1-n-Dodecyl-3-Pyridiniumaldoxime p-Toluenesulfonate

The procedure detailed in Example 3 was substantially repeated, except that p-toluenesulfonic acid was used in place of the hydrogen chloride. 1.7 Grams (0.0037 mol) of the desired product, 1-n-dodecyl-3-pyridiniumaldoxime p-toluenesulfonate (37% yield), were obtained; m.p. 153°–156° C.; ir (KBr) 2900, 1500, 1300, 1220, 1180, 1120, 1030, 1000, 810 and 680 cm$^{-1}$; pmr (d$^6$-DMSO) δ12.2 (s, 1H), 9.4–8.0 (m, 5H), 7.6–7.0 (m, 4H), 4.6 (t, 2H), 2.3 (s, 3H) and 2.7–0.7 (m, 23H) ppm.

Anal. Calcd. for $C_{25}H_{38}N_2OS$: C, 64.89; H, 8.29; N, 6.06. Found: C, 64.98; H, 8.28; N, 5.94.

EXAMPLE 7

Preparation of 1-n-Dodecyl-3-Pyridiniumaldoxime 5-Sulfosalicylate.

The general procedure of Example 3 was repeated using 5-sulfosalicylic acid in place of the hydrogen chloride. 1.5 Grams (0.0029 mol), 29% yield, of 1-n-dodecyl-3-pyridiniumaldoxime 5-sulfosalicylate, m.p. 151°–153° C., were obtained; ir (KBr) 2900, 1660, 1500, 1470, 1230, 1170, 1120, 1000 and 660 cm$^{-1}$; pmr (d$^6$-DMSO) δ9.3–7.7 (m, 7H), 6.9–6.8 (m, 1H), 5.0 (t, 2H) and 2.6–0.7 (m, 23H) ppm.

Anal. Calcd. for $C_{25}H_{36}N_2O_7S$; C, 59.03; H, 7.13; N, 5.51. Found: C, 58.86; H, 7.24; N, 5.56.

The compounds of the present invention dissociate in aqueous solution to form positive

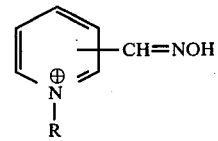

and negative $X^\ominus$ ions. Below the critical micellization concentration or cmc, the ions exist in solution as individual entities. However, above the cmc, the ions are associated into clusters or aggregates known as micelles, the non-polar portions of the molecules (i.e., the long hydrocarbon tail represented by R) being located mainly in the interior of the micelle, and the polar heads of the molecules being at the surface. The surface of the micelle also contains, as reactive sites, —CH=NOH (oxime) groups.

It has been found that one mole of the organophosphorus reagent is consumed per mole of oxime. However, there is a dramatic increase in the rate of reaction coincident with the cmc. This dramatic increase makes possible the rapid detoxification of organophosphate-contaminated areas and equipment and may be an indication of possible utility of the present compounds in the treatment of organophosphate poisoning.

The irreversible reaction of the pyridiniumaldoximes of this invention with a representative organophosphate, diethyl p-nitrophenyl phosphate (Paraoxon®), goes through a compound of the formula

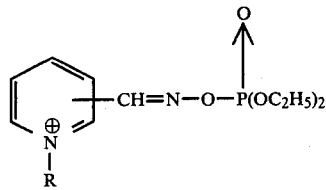

wherein R is as hereinabove defined. That product then rapidly hydrolyzes to non-toxic entities.

The organophosphate pesticides which can be deactivated by the instant micellar reagent include phosphates and thiophosphates. In addition to diethyl p-nitrophenyl phosphate, named supra, such reagents include, but are not limited to, the following: tetrachlorvinphos; dichlorvos (DDVP); tetraethyl pyrophosphate (TEPP); dicrotophos; crotoxyphos; phosphoric acid 1,2-dibromo-2,2-dichloroethyldimethyl ester (naled); phosphamidon; crufomate; monocrotophos; trichlorofon; malathion; carbophenothion; 0,0-dimethyl phosphorochloridothioate; ethion; EPN; methyl parathion; parathion; phorate; ronnel; dioxathion; dimethoate; methyl demeton; demeton O; demeton S; dyfonate; and dicapthon.

Kinetic studies were undertaken to determine the rate of reaction of various concentrations of representative oximes of the present invention with a representative organophosphate pesticide, diethyl p-nitrophenyl phosphate. All reactions were carried out in a carbonate buffer system (prepared using 0.1 M sodium carbonate and 0.1 M sodium bicarbonate) of 0.5 ionic strength (added sodium chloride). [G. E. Delory and E. J. King, Biochem. J., 39, 245 (1945).] The concentration of diethyl p-nitrophenyl phosphate was $3.63 \times 10^{-5}$ M. The formation of the p-nitrophenolate ion was followed spectrophotometrically at 400 nm using a Cary 14 spectrophotometer equipped with an automatic sampling accessory thermostated at 25°±0.2° C.

The reactions were started by adding 25 μl of a 1% v/v solution in dioxane of the phosphate ester to 25 ml of oxime solution equilibrated for one hour at the temperature investigated.

The reactions were followed for a minimum of three half-lives and always obeyed first-order kinetics. Rate constants were calculated from half-lives obtained from semilogarithmic plots of $A_\infty - A_t$ against time ($A_\infty$ is the absorbance at the end point of the reaction and $A_t$ the absorbance at any time t).

A plot of the observed first order rate constants (corrected for hydrolysis) for the reaction of diethyl p-nitrophenyl phosphate with different concentrations of 1-n-heptyl-3-pyridiniumaldoxime iodide (A) and 1-n-dodecyl-3-pyridiniumaldoxime iodide (B) in carbonate-bicarbonate buffer, pH 9.3, $\mu=0.5$ was made. The critical micelle concentration (cmc) for the two oximes in the reaction medium were $2\times 10^{-3}$ M and $6\times 10^{-4}$ M, respectively. There was a linear increase in the observed first order rate constant with increasing concentration of the n-heptyl oxime to approximately $4\times 10^{-2}$ M. The bimolecular rate constant, $k_2' = k_{obs}/[A]$, over the concentration range $(10^{-4} - 4\times 10^{-2})$, was $1.2\times 10^{-2} \pm 0.0008$ $M^{-1}$ $sec^{-1}$. In contrast, there was a marked deviation from linearity in the concentration-rate profile for B. At concentrations of B less than or equal to $2\times 10^{-4}$ M, the bimolecular rate constant for B was equal to that of A within experimental error. At a concentration of B equal to $6\times 10^{-4}$ M, the bimolecular rate constant was equal to $1.5\times 10^{-2}$ $M^{-1}$ $sec^{-1}$. The observed rate increase was coincident with the formation of micelles as evident from the cmc ($6\times 10^{-4}$ M) for B in this medium. A plot of $1/k_o - k_{obs}$ versus $1/C_d - $ Cmc, where $k_o$ is the first order rate constant at the critical micelle concentration, $C_{cmc}$, and $k_{obs}$ is the first order rate constant at the experimental concentration, $C_d$, is linear, correlation coefficient=0.99, as predicted from mathematical micellar models. Values of $K/N$, where K is the binding constant and N is the aggregation number, and $k_m$, the reaction rate constant for the reaction between diethyl p-nitrophenyl phosphate and the n-dodecyl oxime (B) in the micellar phase, calculated from the slope and intercept were 56 $M^{-1}$ and $1.06\times 10^{-2}$ $sec^{-1}$, respectively.

The reaction between diethyl p-nitrophenyl phosphate and the n-dodecyl oxime (B) was also examined for stoichiometry. In nonmicellar reactions, one mole of the organophosphorus agent is consumed per mole of oxime reacting and the reaction rate is dependent upon the oximate ion concentration. The pseudo first order rate constant for the reaction between B and diethyl p-nitrophenyl phosphate (C) was determined at a concentration of B well above its cmc and using a relatively low concentration of C ($[B] \leqq 50$ [C]). In order to establish that the oxime B is a true catalyst or a reagent, the reaction of B with C was followed at a relative concentration of $[B] \simeq 5$ [C]. Following complete destruction of C, an additional quantity of C was added to the reaction mixture and the reaction rate was determined. Under these circumstances, the concentration of B was greater than its cmc, but lowered sufficiently such that the initial rate and the reaction rate were appreciably less than that determined in the first case. After repeating the process several more times, concentrations of B were estimated from the observed second order rate constant. Following this procedure, it was demonstrated that the stoichiometry in the micellar reaction between B and C was 1:1 and that the regeneration of the oxime from the product by hydrolysis was a much slower process. The oxime B is not a true catalyst, but a nucleophillic reagent which deactivates the organophosphate by the formation of the corresponding oxime phosphate.

The influence of pH on the reactivity of 1-n-dodecyl-3-pyridiniumaldoxime iodide with diethyl p-nitrophenyl phosphate is shown in Table I below. The thesis that the reactive species in micellar medium (as in nonmicellar medium) is the oximate ion is substantiated by the fact that the quotient of the observed rate constant corrected for hydrolysis, $k'_{obs}$, and the oximate ion concentration is a constant.

TABLE I

Rates of Reaction of 1-n-Dodecyl-3-Pyridiniumaldoxime Iodide ($2 \times 10^{-3}$M) with Diethyl p-Nitrophenyl Phosphate at Different Solution pH

| pH | $(Ox^-)^* \times 10^3$ | $k_{obs} \times 10^4$ | $k_{obs}' \times 10^4$ | $k_{obs}'/Ox^-$ |
|---|---|---|---|---|
| 8.3 | 0.16 | 2.12 | 2.12 | 1.32 |
| 9.3 | 0.96 | 6.60 | 6.59 | 0.69 |
| 10.6 | 1.88 | 12.7 | 12.6 | 0.67 |
| 11.5 | 1.98 | 14.4 | 13.4 | 0.68 |
| 12.2 | 2.0 | 17.8 | 15.3 | 0.77 |

*Calculated from equation $(Ox^-) = \frac{K_a}{H^+ + K_a}(Ox)_o$, where $K_a = 4.6 \times 10^{-10}$ It has been determined that the main factors affecting the rate of reaction at a given pH include the solubility of the substrate in the micelle, the association constant of the substrate with the micelle and the geometry and aggregation number of the micelle. The latter value is important to the oximate ion concentration as well as to the association constant.

The rates obtained with mixed micelles and cosurfactants as indicated hereinbelow are consistent with the thesis that the dominant factor in determining the rate is the solubility of the substrate in the micelle. In mixtures of 1-n-heptyl-3-pyridiniumaldoxime iodide and 1-n-dodecyl-3-pyridiniumaldoxime iodide which are higher in one component, the "effective cmc" of the mixture will be heavily weighted toward the richer component. It is anticipated that the micelles produced from such mixtures would be very similar to the micelles of the richer component and behave as the micelleof the pure component. For mixtures in which the component compositions do not differ greatly, the micellar component will contain fractions of the two micelles in accordance with Raoults Law and each micelle will contribute to the observed rate.

The effect of mixed micelles on the reaction rate of diethyl p-nitrophenyl phosphate is described in Table II below. In mixtures of 1-n-heptyl- and 1-n-dodecyl-3-pyridiniumaldoxime iodide, where the mole fraction of the mixture is weighted greatly in the direction of the n-heptyl compound, the observed rate is close to that obtained with an equivalent concentration of only the n-heptyl compound. When the mole fraction is weighted greatly toward the n-dodecyl compound, the rate is close to that obtained with an equivalent concentration of the n-dodecyl compound. However, the individual contribution of each component in the micellar phase cannot be ruled out. Thus, when approximately equal concentrations of n-heptyl and n-dodecyl derivatives are used, the rate is equal approximately to the sum of the individual rates.

TABLE II

Half-Lives of Diethyl p-Nitrophenyl Phosphate in Mixtures of 1-n-Heptyl-3-Pyridiniumaldoxime Iodide (A) and 1-n-Dodecyl-3-Pyridiniumaldoxime Iodide (B).

| (A) | (B) | $t_{\frac{1}{2}}$(min.) |
|---|---|---|
| $4 \times 10^{-2}$ | | 40 |
| | $2 \times 10^{-3}$ | 10 |
| $4 \times 10^{-2}$ | $2 \times 10^{-3}$ | 40 |
| $4 \times 10^{-4}$ | | 3090 |
| | $1.4 \times 10^{-3}$ | 28 |
| $4 \times 10^{-4}$ | $1.4 \times 10^{-3}$ | 26 |
| $9.1 \times 10^{-4}$ | | 2238 |
| | $6 \times 10^{-4}$ | 2490 |
| $9.4 \times 10^{-4}$ | $5.9 \times 10^{-4}$ | 1273 |

The results for the effect of added surfactants on the rate, also set forth below, are consistent with the hypothesis that the reaction rate is directly proportional to the amount of substrate incorporated into the micelle and that the amount is directly proportional to the micellar volume. To a solution containing $1 \times 10^{-3}$ M 1-n-dodecyl-3-pyridiniumaldoxime iodide, the micellar concentration of 1-n-dodecyl-3-pyridiniumaldoxime iodide is approximately $4 \times 10^{-4}$ M. Addition of $3 \times 10^{-3}$ M CTAB (cetyltrimethylammonium bromide) to the solution provides an additional micellar concentration of approximately $5 \times 10^{-4}$ M. Thus, the contribution of the added CTAB more than doubles the micellar volume and a corresponding increase in the reaction rate is observed. For a solution containing $3 \times 10^{-3}$ M 1-n-dodecyl-3-pyridiniumaldoxime iodide, the percentage increase in micellar volume upon the addition of CTAB is less and likewise, its effect upon the reaction rate is decreased.

The effect of additional cosurfactants, CTAB or Brij (polyoxyethylene 20 cetyl ether), at a constant concentration of $3 \times 10^{-3}$ M, on the first order rate constants of the reaction of diethyl p-nitrophenyl phosphate with different concentrations of 1-n-dodecyl-3-pyridiniumaldoxime iodide was determined. At a concentration of 1-n-dodecyl-3-pyridiniumaldoxime iodide equal to $1 \times 10^{-4}$ M, the addition of CTAB increased the rate by a factor of 82. At a concentration of the n-dodecyl compound equal to $1 \times 10^{-3}$ M, the increase was a factor of 3 and at a concentration of $3 \times 10^{-3}$ M, the rate increase was less than 2. Similar quantitative data were obtained when Brij was used as the cosurfactant. The relative rate increase thus tends to decrease with increasing concentrations of the n-dodecyl compound. It can be seen from the data obtained that a known non-toxic surfactant can be advantageously used in conjunction with a compound of formula (I) or (II) to form a micellar medium capable of deactivating/detoxifying organophosphates.

In addition to the studies indicated above, various physical-chemical parameters of the compounds of the invention were investigated, as indicated below:

a. Solubility

Various weights of each oxime were placed in screw-capped 2 dram glass vials; 7 ml quantities of the appropriate buffer solution were added and the vials sealed (Teflon liners). They were then shaken in a water bath thermostated at 25° C. for periods up to seven days. Samples were taken at various intervals to insure that equilibrium conditions had been attained.

At 25° C., samples were filtered using a Millipore Swinnex adaptor (Millipore HAWD01300 0.45 $\mu$m filter), and diluted in a vehicle of ethanol/pH 9.3 carbonate buffer (50:50 v/v) to approximately $0.1-1 \times 10^{-4}$ M. The absorbance of the resulting solutions at 290 nm or 295 nm were measured and the solubilities calculated based on the respective molar absorptivities:

1-n-heptyl-3-pyridiniumaldoxime iodide, $\epsilon_{295} = 1.21 \times 10^4$ M$^{-1}$ cm$^{-1}$;

1-n-dodecyl-3-pyridiniumaldoxime iodide, $\epsilon_{295} = 1.29 \times 10^4$ M$^{-1}$ cm$^{-1}$;

1-n-dodecyl-3-pyridiniumaldoxime chloride, $\epsilon_{290} = 1.17 \times 10^4$ M$^{-1}$ cm$^{-1}$;

1-n-dodecyl-3-pyridiniumaldoxime bromide, $\epsilon_{290} = 1.22 \times 10^4$ M$^{-1}$ cm$^{-1}$;

1-n-dodecyl-3-pyridiniumaldoxime methanesulfonate, $\epsilon_{290} = 1.07 \times 10^4$ M$^{-1}$ cm$^{-1}$;

1-n-dodecyl-3-pyridiniumaldoxime p-toluenesulfonate, $\epsilon_{290} = 1.03 \times 10^4$ M$^{-1}$ cm$^{-1}$; and 1-n-dodecyl-3-pyridiniumaldoxime 5-sulfosalicylate, $\epsilon_{290} = 1.54 \times 10^4$ M$^{-1}$ cm$^{-1}$.

b. Critical Micelle Concentration (cmc)

A concentrated solution of each oxime in buffer [G. E. Delory and E. J. King, Biochem. J. 39, 245 (1945)] was prepared, assayed and serially diluted to produce a range of concentrations. The solutions were equilibrated at 25°±0.2° C. Using a Hitachi Perkin-Elmer MPF-2A spectrophotofluorimeter to excite the solutions at a wavelength of 410 nm, the intensity of the Raman peak of water occurring at 478 nm was recorded. This intensity was plotted against oxime concentration and the inflection point in curve determined the critical micelle concentration (cmc). The critical micelle concentration of 1-n-heptyl-3-pyridiniumaldoxime iodide was found to be $1.95 \times 10^{-3}$ M, while that of 1-n-dodecyl-3-pyridiniumaldoxime iodide was $6.30 \times 10^{-4}$ M.

c. pK$_a$ Determination of 1-n-Dodecyl-3-Pyridiniumaldoxime Iodide

The pK$_a$ of 1-n-dodecyl-3-pyridiniumaldoxime iodide above and below the critical micelle concentration (cmc) and in the presence of $3 \times 10^{-3}$ M cetyltrimethylammonium bromide (CTAB) and Brij were determined spectrophotometrically. Carbonate-bicarbonate buffers ranging in pH from 5.8 to 12.8 were prepared and used to prepare the following solutions: (1) $5 \times 10^{-5}$ M oxime, below cmc; (2) $2 \times 10^{-3}$ M oxime, above cmc; (4) $5 \times 10^{-5}$ M oxime in $3 \times 10^{-3}$ M CTAB and (4) $5 \times 10^{-5}$ M oxime in $3 \times 10^{-3}$ M Brij.

The absorption spectra of these solutions were determined from 220 to 450 nm. The absorbance at 295 nm was plotted against the pH of the buffer solutions. Sigmoidal curves were obtained and the pK$_a$ values were calculated based on three determinations around the point of half neutralization using the equation $$pK_a = pH_{obsd} + \log \frac{[A\text{max} + A\text{obsd}]}{[A\text{obsd} + A\text{min}]}$$

where Amax, Amin and Aobsd are the absorbance values for the dissociated, undissociated and the partly dissociated (at pH$_{obsd}$) solutions of the oxime. Results are tabulated below.

TABLE III

The pK$_a$ of 1-n-Dodecyl-3-Pyridiniumaldoxime Iodide at 25° C. Under Different Conditions

| Oxime Concentration | Conditions | pK$_a$ ± S. E. |
|---|---|---|
| 5 × 10$^{-5}$ M | Below CMC | 9.18 ± 0.07 |
| 2 × 10$^{-3}$ M | Above CMC | 9.34 ± 0.1 |
| 5 × 10$^{-5}$ M | 3 × 10$^{-3}$ M CTAB added* | 9.15 ± 0.03 |
| 5 × 10$^{-5}$ M | 3 × 10$^{-3}$ M Brij added | 9.65 ± 0.15 |

*CMC of CTAB is 2.5 × 10$^{-3}$ M.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims.

What we claim is:

1. A compound of the formula

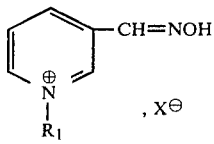

wherein R$_1$ is a radical of the type -(alkylene-O)$_n$-alkyl wherein n is a number from 0 to 4 inclusive and the alkylene and alkyl portions together contain from 6 to 25 carbon atoms, with the proviso that R$_1$ has a total of at least 7 atoms in its longest chain, and wherein X$^\ominus$ is an anion derived from a non-toxic inorganic or organic base.

2. A compound according to claim 1 wherein R$_1$ is an alkyl radical containing 7 to 25 carbon atoms and having at least 7 carbon atoms in its longest chain.

3. A compound according to claim 1 or 2 wherein X$^\ominus$ is an anion selected from the group consisting of halides, 5-sulfosalicylates and radicals of the formula —R$_2$SO$_3$$^\ominus$ wherein R$_2$ is C$_1$-C$_{20}$ alkyl, phenyl, substituted phenyl or naphthyl.

4. A compound according to claim 3 wherein X$^\ominus$ is an anion selected from the group consisting of iodide, chloride, bromide, methanesulfonate, p-toluenesulfonate and 5-sulfosalicylate.

5. The compound according to claim 1 which is 1-n-heptyl-3-pyridiniumaldoxime iodide.

6. The compound according to claim 1 which is 1-n-dodecyl-3-pyridiniumaldoxime iodide.

7. The compound according to claim 1 which is 1-n-dodecyl-3-pyridiniumaldoxime chloride.

8. The compound according to claim 1 which is 1-n-dodecyl-3-pyridiniumaldoxime bromide.

9. The compound according to claim 1 which is 1-n-dodecyl-3-pyridiniumaldoxime methanesulfonate.

10. The compound according to claim 1 which is 1-n-dodecyl-3-pyridiniumaldoxime p-toluenesulfonate.

11. The compound according to claim 1 which is 1-n-dodecyl-3-pyridiniumaldoxime 5-sulfosalicylate.

12. A method for the detoxification of an organophosphate-contaminated portion of the environment which comprises contacting said organophosphate with a micellar medium comprising a compound of the formula wherein R is an organic residue capable of providing micellar characteristics of the molecule and X$^\ominus$ is an anion derived from a non-toxic inorganic or organic acid, with the proviso that R has a total of at least 7 atoms in its longest chain.

13. A method according to claim 12 wherein X$^\ominus$ is an anion selected from the group consisting of halides, 5-sulfosalicylates and radicals of the formula —R$_2$SO$_3$$^\ominus$ wherein R$_2$ is C$_1$-C$_{20}$ alkyl, phenyl, substituted phenyl or naphthyl.

14. A method according to claim 13 wherein X$^\ominus$ is an anion selected from the group consisting of iodide, chloride, bromide, methanesulfonate, p-toluenesulfonate and 5-sulfosalicylate.

15. A method according to claim 12, 13 or 14 wherein R is a radical of the type —(alkylene-O)$_n$-alkyl wherein n is a number from 0 to 4 inclusive and the alkylene and alkyl portions together contain from 6 to 25 carbon atoms, with the proviso that R has a total of at least 7 atoms in its longest chain.

16. A method according to claim 15 wherein R is an alkyl radical containing 7 to 25 carbon atoms and having at least 7 carbon atoms in its longest chain.

17. A method according to claim 12 wherein the compound is 1-n-heptyl-3-pyridiniumaldoxime iodide.

18. A method according to claim 12 wherein the compound is selected from the group consisting of 1-n-dodecyl-3-pyridiniumaldoxime iodide, 1-n-dodecyl-3-pyridiniumaldoxime chloride, 1-n-dodecyl-3-pyridiniumaldoxime bromide, 1-n-dodecyl-3-pyridiniumaldoxime methanesulfonate, 1-n-dodecyl-3-pyridiniumaldoxime p-toluenesulfonate and 1-n-dodecyl-3-pyridiniumaldoxime 5-sulfosalicylate.

19. A method according to claim 12 wherein the micellar medium additionally comprises a known non-toxic surfactant.

20. A method of claim 18 wherein the compound is 1-n-dodecyl-3-pyridiniumaldoxime iodide.

* * * * *